(12) United States Patent
Mathur et al.

(10) Patent No.: US 7,145,040 B2
(45) Date of Patent: Dec. 5, 2006

(54) PROCESS FOR THE PREPARATION OF AMINO ACIDS USEFUL IN THE PREPARATION OF PEPTIDE RECEPTOR MODULATORS

(75) Inventors: Arvind Mathur, Bridgewater, NJ (US); K. Selva Kumar, Tamil Nadu (IN)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 11/172,488

(22) Filed: Jun. 30, 2005

(65) Prior Publication Data

US 2006/0004222 A1 Jan. 5, 2006

Related U.S. Application Data

(60) Provisional application No. 60/584,968, filed on Jul. 2, 2004.

(51) Int. Cl.
C07F 5/02 (2006.01)
C07C 229/00 (2006.01)

(52) U.S. Cl. .................. 568/1; 568/6; 562/7; 562/444; 562/447; 562/448

(58) Field of Classification Search .................... 568/1, 568/6; 562/443, 448, 7, 447, 444
See application file for complete search history.

(56) References Cited

U.S. PATENT DOCUMENTS

| | | | |
|---|---|---|---|
| 3,674,836 A | 7/1972 | Cregar | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,647,576 A | 3/1987 | Hoefle et al. | |
| 4,681,893 A | 7/1987 | Roth | |
| 4,686,237 A | 8/1987 | Anderson | |
| 4,759,923 A | 7/1988 | Buntin et al. | |
| 4,871,721 A | 10/1989 | Biller | |
| 4,924,024 A | 5/1990 | Biller | |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,354,772 A | 10/1994 | Kathawala | |
| 5,385,929 A | 1/1995 | Bjorge et al. | |
| 5,488,064 A | 1/1996 | Sher | |
| 5,491,134 A | 2/1996 | Sher et al. | |
| 5,506,219 A | 4/1996 | Robl | |
| 5,541,204 A | 7/1996 | Sher et al. | |
| 5,594,016 A | 1/1997 | Ueno et al. | |
| 5,595,872 A | 1/1997 | Wetterau, II et al. | |
| 5,612,359 A | 3/1997 | Murugesan | |
| 5,614,492 A | 3/1997 | Habener | |
| 5,686,104 A | 11/1997 | Mills et al. | |
| 5,691,322 A | 11/1997 | Robl | |
| 5,712,279 A | 1/1998 | Biller et al. | |
| 5,712,396 A | 1/1998 | Magnin et al. | |
| 5,739,135 A | 4/1998 | Biller et al. | |
| 5,753,675 A | 5/1998 | Wattanasin | |
| 5,760,246 A | 6/1998 | Biller et al. | |
| 5,770,615 A | 6/1998 | Cheng et al. | |
| 5,776,983 A | 7/1998 | Washburn et al. | |
| 5,827,875 A | 10/1998 | Dickson, Jr. et al. | |
| 5,885,983 A | 3/1999 | Biller et al. | |
| 5,962,440 A | 10/1999 | Sulsky | |
| 5,998,375 A | 12/1999 | Thøgersen et al. | |
| 6,043,265 A | 3/2000 | Murugesan et al. | |
| 6,545,029 B1* | 4/2003 | Vaupel | ....................... 514/357 |
| 6,548,667 B1 | 4/2003 | Park et al. | |
| 6,737,417 B1 | 5/2004 | Jo et al. | |
| 7,045,652 B1* | 5/2006 | Caron et al. | .................... 562/7 |
| 2003/0195157 A1 | 10/2003 | Natarajan et al. | |
| 2004/0127423 A1 | 7/2004 | Natarajan et al. | |

FOREIGN PATENT DOCUMENTS

| | | |
|---|---|---|
| EP | 0 142 146 | 5/1985 |
| EP | 0 221 025 | 5/1987 |
| FR | 2 596 393 | 10/1987 |
| GB | 2 205 837 | 12/1988 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |

(Continued)

OTHER PUBLICATIONS

U.S. Appl. No. 11/170,968, filed Jun. 30, 2005, Ewing et al.

(Continued)

Primary Examiner—Shailendra Kumar
(74) Attorney, Agent, or Firm—Brian C. Carey; Briana C. Bergen

(57) ABSTRACT

The present invention provides process useful for the preparation of intermediates which are useful in the preparation of amino acids useful in preparing peptide receptor modulators, for example agonists or partial agonists of such peptide receptors. Such peptide receptor modulators include, for example glucagon like peptide-1 receptor modulators which are useful for the amelioration of the diabetic condition.

3 Claims, No Drawings

FOREIGN PATENT DOCUMENTS

| | | |
|---|---|---|
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |

OTHER PUBLICATIONS

Ashworth, D.M. et al., "2-Cyanopyrrolidides as Potent, Stable Inhibitors of Dipeptidyl Peptidase IV", Bioorganic & Medical Chemistry Letters, vol. 6, No. 10, pp. 1163-1166 (1996).

Ashworth, D.M. et al., "4-Cyanothiazolidides as Very Potent, Stable Inhibitors of Dipeptidyl Peptidase IV", Bioorganic & Medicinal Chemistry Letters, vol. 6, No. 22, pp. 2745-2748 (1996).

Atherton, E. et al., Chapter 1: "The Fluorenylmethoxycarbonyl Amino Protecting Group", The Peptides: Analysis, Synthesis, Biology, vol. 9: Special Methods in Peptide Synthesis, Part C, Academic Press, Inc., publ., Udenfriend, S. et al., eds. pp. 1-38 (1987).

Barany, G. et al., Chapter 1: "Solid-Phase Peptide Synthesis", The Peptides: Analysis, Synthesis, Biology, vol. 2: Special Methods in Peptide Synthesis, Part A, Acdemic Press, Inc., publ. Gross, E. et al., eds., pp. 1-284 (1979).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Burgess, K. et al., "Solid Phase Syntheses of Oligoureas", J. Am. Chem. Soc., vol. 119, No. 7, pp. 1556-1564 (1997).

Byrne, M.M. et al., "Inhibitory effects of hyperglycaemia on fed jejunal motility: potential role of hyperinsulineamia", European Journal of Clinical Investigation, vol. 28, pp. 72-78 (1998).

Capson, T.L., "Synthesis and Evaluation of Ammonium Analogs of Carbocationic Intermediates in Squalence Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreative Analogs of Terpenoid Pyrophosphates to Studies of Multistep Biosynthesis. Demonstration That 'Presqualene Pyrophosphate' Is an Essential Intermediate on the Path to Squalene", Journal of the American Chemical Society, vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Davern, P. et al., "Chemical and Biological Reactivity of Sulfamidopenicillins", J. Chem. Soc. Perkin Trans. 2, pp. 381-387 (1994).

Fehder, W.P. et al., "Development and Evaluation of a Chromatographic Procedure for Partial Purification of Substance P with Quantitation by an Enzyme Immunoassay", Clinical and Diagnositc Laboratory Immunology, vol. 5, No. 3, pp. 303-307 (1998).

Fehrentz, J.-A. et al., "An Efficient Synthesis of Optically Active α-(t-Butoxycarbonylamino)-aldehydes from α-Amino Acids", Synthesis, pp. 676-678 (1983).

Fingl, E. et al., Section I: "Introduction", Chapter I: "General Principles", The Pharmacological Basics of Therapeutics, 5th Ed., Macmillan Publishing Co., Inc., publ., Goodman, L.S. et al., eds., pp. 1-46 (1975).

Flint, A. et al., "Glucagon-like Peptide 1 Promotes Satiety and Suppresses Energy Intake in Humans", J. Clin. Invest., vol. 101, No. 3, pp. 515-520 (1998).

Gennaro, A.R., ed., Remington's Pharmaceutical Sciences, 18th Ed., Mack Publishing Company, publ., pp. xv-xvi (table of contents) (1990).

Gennaro, A.R., ed., Remington: Practice of the Science and Pharmacy, 19th Ed., Mack Publishing Company, publ., pp. xv-xvi (table of contents) (1995).

Gennaro, A.R., ed., Remington: Practice of the Science and Pharmacy, vol. II, 19th Ed., Mack Publishing Company, publ., pp. vii-viii (table of contents) (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Gluschankof, P. et al., "Enzymes processing somatostatin precursors: An Arg-Lys esteropeptidase from the rat brain cortex converting somatostatin-28 into somatostatin-14", Proc. Natl. Acad. Sci. USA, vol. 81, pp. 6662-6666 (1984).

Gutzwiller, J.-P. et al., "Glucagon-like peptide-1: a potent regulator of food intake in humans", Gut, vol. 44, pp. 81-86 (1999).

Hara, S. "Ileal $Na^+$/bile acid cotrasporter inhibitors", Drugs of the Future, vol. 24, No. 4, pp. 425-430 (1999).

Holst, J.J., "Glucagon-like Peptide-1, A Gastrointestinal Hormone with a Pharmaceutical Potential", Current Medicinal Chemistry, vol. 6, No. 11, pp. 1005-1017 (1999).

Ito, Y. et al., "Difference in cholesterol-binding and cytolytic activities between listeriolysin O and seeligeriolysin O: a possible role of alanine residue in tryptophan-rich undecapeptide", FEMS Microbiology Letters, vol. 203, pp. 185-189 (2001).

Johannsson, G. et al., "Growth Hormone Treatment of Abdominally Obese Men Reduces Abdominal Fat Mass, Improve Glucose and Lipoprotein Metabolism, and Reduces Diastolic Blood Pressure", Journal of Clinical Endocrinology and Metabolism, vol. 82, No. 3, pp. 727-734 (1997).

King, D.S. et al., "A cleavage method which minimizes side reactions following Fmoc solid phase peptide synthesis", Int. J. Peptide Protein Res., vol. 36, pp. 255-266 (1990).

Krause, B.R. et al., Chapter 6: ACAT Inhibitors: "Physiological Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ: Effect of PPAR-α Activation on Abnormal Lipid Metabolism in Liver of Zucker Fatty Rats", Diabetes, vol. 47, pp. 1841-1847 (1998).

Näslund, E. et al., "Energy intake and appetite are suppressed by glucagon-like peptide-1 (GLP-1) in obese men", International Journal of Obesity, vol. 23, pp. 304-311 (1999).

Nicolosi, R.J. et al., "The ACAT inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pryophosphate Analogues", Journal of Medicinal Chemistry, vol. 20, No. 2, pp. 243-249 (1977).

Rosenblum, S.B. et al., "Discovery of 1-(4-Fluorophenyl)-(3R)-[3-(4-fluorophenyl)-(3S)-(4-hydroxyphenyl](4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sobera, L.A. et al., "Avasimibe: Treatment of Lipoprotein Disorders—ACAT Inhibitor", Drugs of the Future, vol. 24, No. 1, pp. 9-15 (1999).

Stewart, J.M. et al., Solid Phase Peptide Synthesis, 2nd Ed., Pierce Chemical Company, publ., pp. vii-xi (table of contents), 92 (1984).

Stoffers, D.A. et al., "Insulinotropic Glucagon-Like Peptide 1 Agonist Stimulate Expression of Homeodomain Protein IDX-1 and Increase Islet Size in Mouse Pancreas", Diabetes, vol. 49, pp. 741-748 (2000).

Stout, D.M. et al., "Inhibitors of Acyl-CoA: Cholesterol O-Acyl Transferase (ACAT) as Hypocholesterolemic Agents. 6. The First Water-Soluble ACAT Inhibitor with Lipid-Regulating Activity. Inhibitors of Acyl-CoA:Cholesterol Acyltransferase (ACAT). 7. Development of a Series of Substituted N-Phenyl-N'-[(1-phenylcyclopentyl)-methyl]ureas with Enhanced Hypocholestrolemic Activity", Chemtracts—Organic Chemistry, vol. 8, pp. 359-362 (1995).

Wettergen, A. et al., "Truncated GLP-1 (Proglucagon 78-107-Amide) Inhibits Gastric and Pancreatic Functions in Man", Digestive Diseases and Sciences, vol. 38, No. 4, pp. 656-673 (1993).

Yamada, M. et al., "A Potent Dipeptide Inhibitor of Dipeptidyl Peptidase IV", Bioorganic & Medicinal Chemistry Letters, vol. 8, pp. 1537-1540 (1998).

* cited by examiner

PROCESS FOR THE PREPARATION OF AMINO ACIDS USEFUL IN THE PREPARATION OF PEPTIDE RECEPTOR MODULATORS

This application claims priority to U.S. Provisional Patent Application Ser. No. 60/584,968, filed Jul. 2, 2004 of which is hereby incorporated by reference in its entirety.

FIELD OF THE INVENTION

The present invention provides process useful for the preparation of intermediates which are useful in the preparation of amino acids useful in preparing peptide receptor modulators, for example agonists or partial agonists of such peptide receptors. Such peptide receptor modulators include, for example glucagon like peptide-1 receptor modulators which are useful for the amelioration of the diabetic condition.

BACKGROUND OF THE INVENTION

It is desirable to develop peptide receptor modulators which may be useful for affecting the native activity of such a receptor and thus for affecting the biological pathways in which such a receptor is involved.

For example, GLP-1 is an important gut hormone with regulatory function in glucose metabolism and gastrointestinal secretion and metabolism, and has been identified as a very potent and efficacious stimulator for insulin release. Therefore, it is desirable to develop modulators of peptide receptors, for example the GLP-1 receptor, which will affect the native activity of the receptor to effect a desired biological response.

The present invention therefore provides a novel process for the preparation of intermediates useful in the preparation of amino acid which may be used in preparing peptide receptor modulators, for example GLP-1 receptor modulators, including agonists or partial agonists.

SUMMARY OF THE INVENTION

In one aspect, the present invention is directed to a process for the preparation of a compound of Formula I:

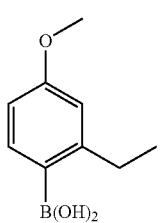

I the process comprising the steps of:
methylation of 3-ethylphenol to produce 3-ethylanisole;
bromination of the 3-ethylanisole at a position para to a methoxy group to produce 4-bromo-3-ethyl anisole;
conversion of the 4-bromo-3-ethyl anisole, the conversion comprising (a) reacting the 4-bromo-3-ethyl anisole with n-butyl lithium to produce the lithium salt of the corresponding anion of the 4-bromo-3-ethyl anisole; (b) reacting the lithium salt of the anion of the 4-bromo-3-ethyl anisole with triethyl borate; and (c) quenching with aqueous acid.

In another aspect, the present invention is directed to a process for the preparation of a compound of Formula I:

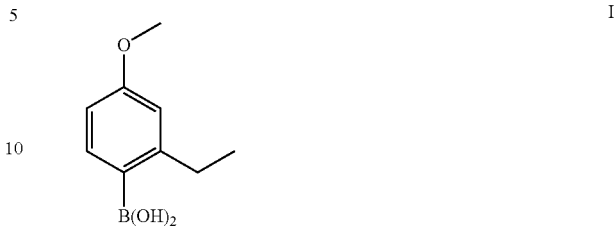

I according to Scheme 1, as follows:

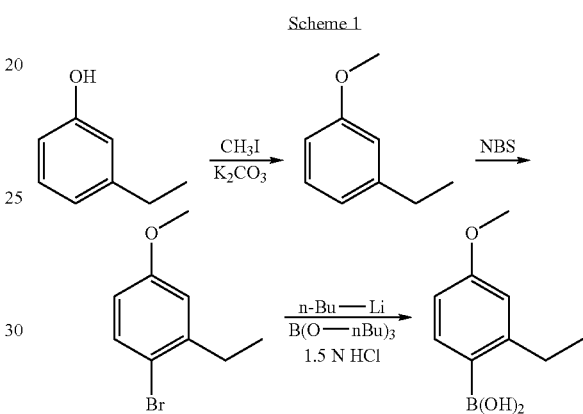

In another aspect, the present invention is directed to a process for the preparation of a compound of Formula II:

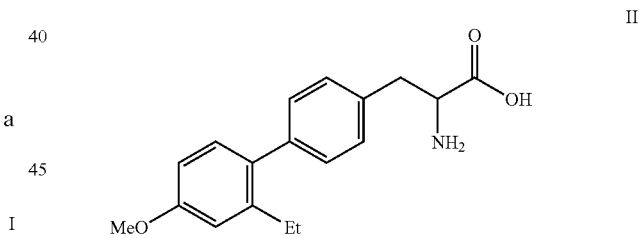

II the process comprising the steps of:
methylation of 3-ethylphenol to produce 3-ethylanisole;
bromination of the 3-ethylanisole at a position para to a methoxy group to produce 4-bromo-3-ethyl anisole;
conversion of the 4-bromo-3-ethyl anisole, the conversion comprising (a) reacting the 4-bromo-3-ethyl anisole with n-butyl lithium to produce the lithium salt of the corresponding anion of the 4-bromo-3-ethyl anisole; (b) reacting the lithium salt of the anion of the 4-bromo-3-ethyl anisole with tri-n-butyl borate; (c) quenching with aqueous acid;
reacting the resultant 2-ethyl-4-methoxy-phenylboronic acid with the triflic anhydride of a suitably protected tyrosine amino acid in the presence of a Palladium catalyst (Suzuki coupling); and
removing the carboxyl protecting group from the resulting biphenyl amino acid to yield the amino-protected amino acid useful for incorporation into a peptide receptor modulator.

In another aspect, the present invention is directed to a process for the preparation of a compound of Formula II:

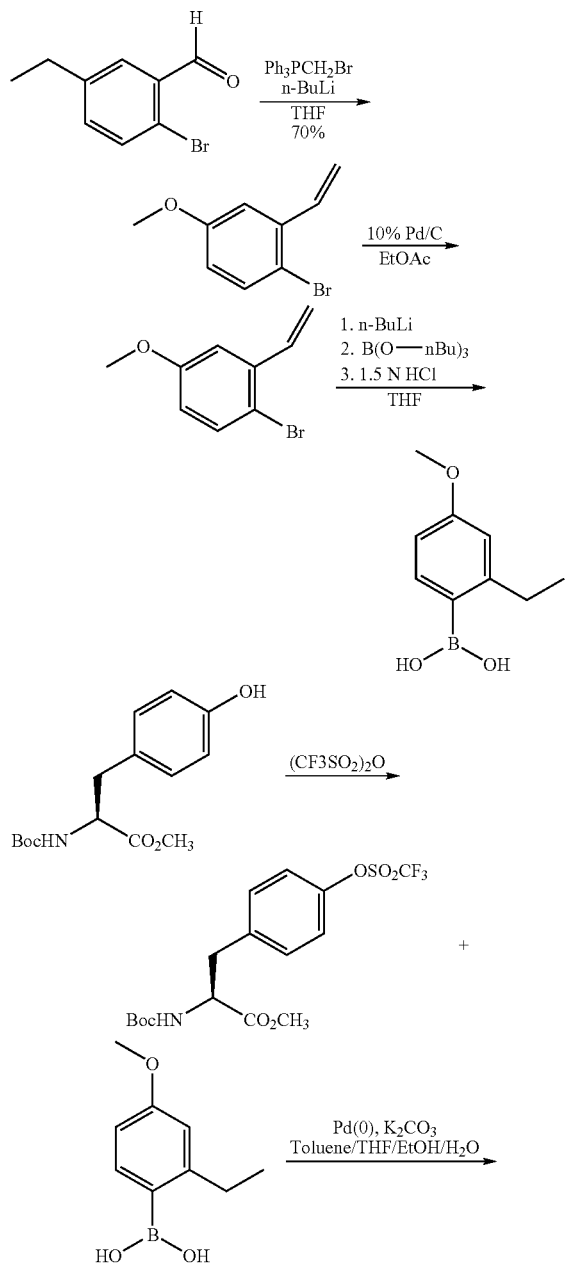

according to Scheme 2, as follows:

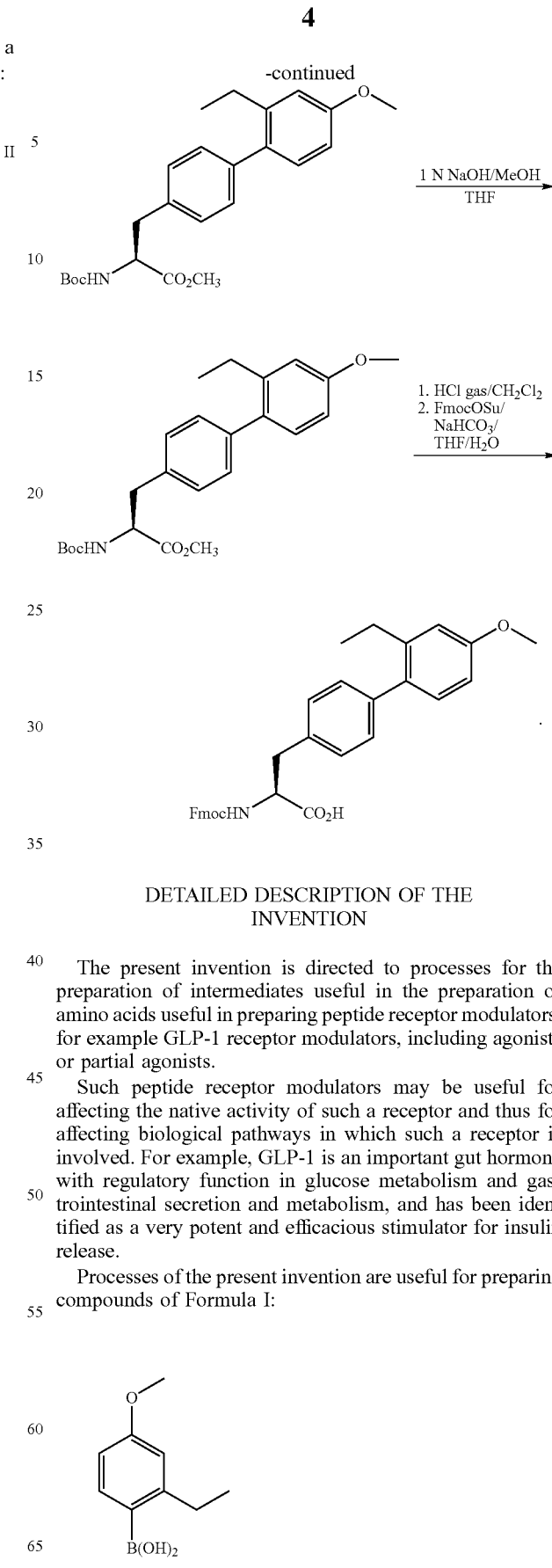

DETAILED DESCRIPTION OF THE INVENTION

The present invention is directed to processes for the preparation of intermediates useful in the preparation of amino acids useful in preparing peptide receptor modulators, for example GLP-1 receptor modulators, including agonists or partial agonists.

Such peptide receptor modulators may be useful for affecting the native activity of such a receptor and thus for affecting biological pathways in which such a receptor is involved. For example, GLP-1 is an important gut hormone with regulatory function in glucose metabolism and gastrointestinal secretion and metabolism, and has been identified as a very potent and efficacious stimulator for insulin release.

Processes of the present invention are useful for preparing compounds of Formula I:

which are useful in the preparation of amino acids of Formula II:

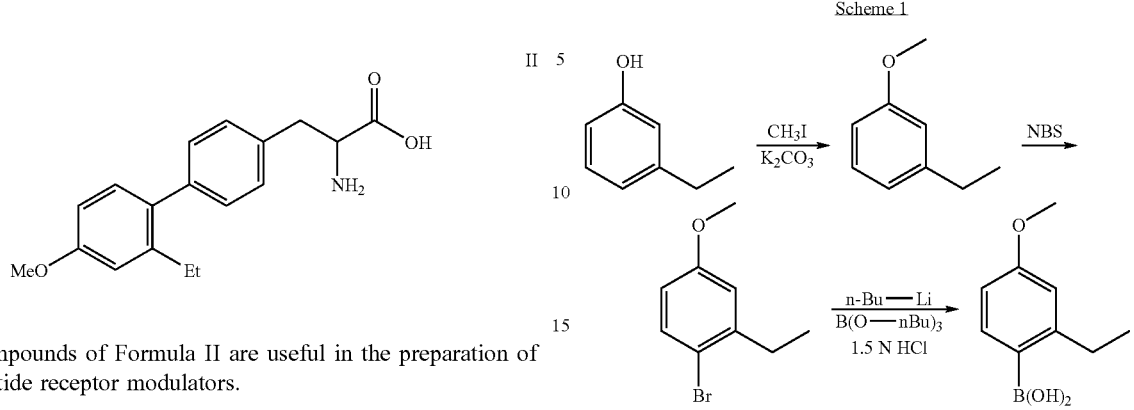

Compounds of Formula II are useful in the preparation of peptide receptor modulators.

EXAMPLE 1

Synthesis of (2-Ethyl-4-methoxy)phenyl boronic acid (2-Ethyl-4-methoxy)phenyl boronic acid (Formula I) was prepared as follows, and as shown in Scheme 1: (1) methylation of 3-ethylphenol to produce 3-ethylanisole; (2) bromination of the 3-ethylanisole at a position para to a methoxy group to produce 4-bromo-3-ethyl anisole; (3) conversion of the 4-bromo-3-ethyl anisole, the conversion comprising (a) reacting the 4-bromo-3-ethyl anisole with n-butyl lithium to produce the lithium salt of the corresponding anion of the 4-bromo-3-ethyl anisole; (b) reacting the lithium salt of the anion of the 4-bromo-3-ethyl anisole with tri-n-butyl borate; and (c) quenching with aqueous acid.

Specifically, To a mixture of 3-Ethylphenol (50 g, 0.4 mol, 98% pure, Fluka) and $K_2CO_3$ (283 g, 2.05 mol) in dry acetone (500 ml) was added methyliodide (290 g, 2.05 mol). The reaction mixture was transferred to an autoclave and refluxed at 70° C. overnight. The reaction mixture was filtered through a Celite pad. The pad was washed with acetone and the combined filtrate and washes were concentrated. The product was dissolved in DCM, filtered and evaporated to dryness. Yield: 50 g, 90%, as a brown liquid.

3-Ethylanisole (50 g, 0.3676 mol) and N-bromosuccinimide (72 g, 0.4 mol) in acetonitrile (1 L) were stirred for 8 hr under dark at RT. The reaction mixture was concentrated below 40° C. and the residue obtained was redissolved in $CCl_4$ and filtered. The filtrate was concentrated and the product was purified by fractional distillation. Yield: 35 g, 43%, as pale yellow liquid.

A solution of 4-bromo-3-ethyl anisole (94 g, 0.437 mol) in THF (900 ml) was cooled to −78° C. n-Butyl lithium (249 ml, 0.55 mol) was added dropwise at the same temperature. Stirring was continued for 1 hr at −78°0 C. Tri-n-butyl borate (177 ml, 0.655 mol) was added slowly at −78° C. The cooling bath was removed, the reaction mixture was allowed to warm to 0° C. and was quenched with 1.5 N hydrochloric acid at 0° C. The organic layer was separated. The aqueous layer was extracted with ethylacetate and the combined organic layers were washed with brine and concentrated. The residue obtained was stirred in pet-ether for 30 min. The solid obtained was filtered and dried under vacuum. Yield: 65 g, 82%, as a white solid.

EXAMPLE 2

Amino Acid Synthesis

The resultant (2-Ethyl-4-methoxy)phenyl boronic acid was used to prepare the amino acid of Formula II, according to Scheme 2:

-continued

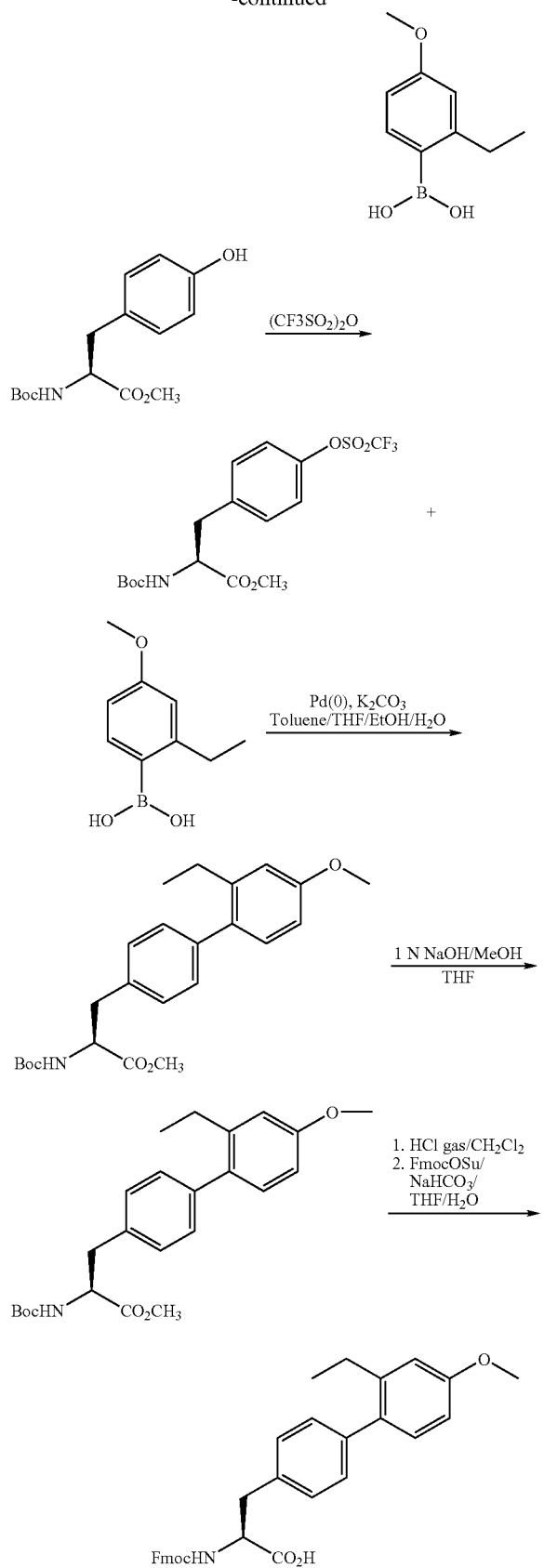

EXAMPLE III

Peptide Receptor Modulator Synthesis

Peptide receptor modulators which may be thus produced by a compound of Formula II (Example III) includes a GLP-1 receptor modulator of Formula III:

$$X_{aa1}-X_{aa2}-X_{aa3}-X_{aa4}-X_{aa5}-X_{aa6}-X_{aa7}-X_{aa8}-X_{aa9}-X_{aa10}-X_{aa11} \quad (III)$$

wherein,
$X_{aa1}$ is H;
$X_{aa2}$ is Aib;
$X_{aa3}$ is E;
$X_{aa4}$ is G;
$X_{aa5}$ is a T;
$X_{aa6}$ is L-α-Me-Phe(2-Fluoro);
$X_{aa7}$ is T;
$X_{aa8}$ is S;
$X_{aa9}$ is D;
$X_{aa10}$ is a compound of Formula II; and
$X_{aa11}$ is 4-(2'-methylphenyl)-3-pyridylalanine-NH2.

Where the above amino acid abbreviations refer to those commonly understood in the art.

Peptide receptor modulators produced from intermediate prepared by processes of the present invention may be prepared by any suitable manner recognized by one of skill in the art of peptide chemistry. For example, the peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) as described herein and, after completion of the peptide sequence assembly, the resulting peptide alcohol is released with LiBH4 in THF (see J. M. Stewart and J. D. Young, supra, p. 92). Also, a peptide synthesizer may be used, for example an Advanced Chemtech Multiple Peptide Synthesizer (MPS396) or an Applied Biosystems Inc. peptide synthesizer (ABI 433A).

The following abbreviations may be used herein:

| | |
|---|---|
| Ph = phenyl | DMF = N,N-dimethylformamide |
| Bn = benzyl | EtOAc = ethyl acetate |
| i-Bu = iso-butyl | THF = tetrahydrofuran |
| i-Pr = iso-propyl | TFA = trifluoroacetic acid |
| Me = methyl | NMP = N-methylpyrrolidone |
| Et = ethyl | DCM = dichloromethane |
| Pr = n-propyl | n-BuLi = n-butyllithium |
| Bu = n-butyl | Pd/C = palladium on carbon |
| TMS = trimethylsilyl | TEA = triethylamine |
| Et$_2$O = diethyl ether | min = minute(s) |
| HOAc or AcOH = acetic acid | h or hr = hour(s) |
| | L = liter |
| MeCN = acetonitrile | mL or ml = milliliter |
| | μl = microliter |
| g = gram(s) | rt = room temperature |
| mg = milligram(s) | sat or sat'd = saturated |
| mol = mole(s) | aq. = aqueous |
| mmol = millimole(s) | mp = melting point |
| meq = milliequivalent | Bip = biphenylalanine |
| LiBH$_4$ = lithium borohydride | |
| DIEA = Diisopropylethylamine | |
| FMOC = fluorenylmethoxycarbonyl | |

-continued

Boc or BOC = tert-butoxycarbonyl
NBS = N-Bromosuccinimide
TLC = thin layer chromatography
HPLC = high performance liquid chromatography
LC/MS = high performance liquid chromatography/mass spectrometry
MS or Mass Spec = mass spectrometry
NMR = nuclear magnetic resonance One of skill in the art of peptide chemistry is aware that amino acid residues occur as both D and L isomers, and that the present invention includes the use of either or a mixture of isomers for amino acid residues incorporated in the synthesis of the peptides described herein.

The present invention is not to be limited in scope by the specific embodiments described that are intended as single illustrations of individual aspects of the invention. Functionally equivalent methods and components in addition to those shown and described herein will become apparent to those skilled in the art from the foregoing description and accompanying drawings. Such modifications are intended to fall within the scope of the appended claims.

What is claimed is:

1. A process for the preparation of a compound of Formula I:

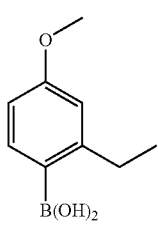

I said process comprising the steps of:
methylation of 3-ethylphenol to produce 3-ethylanisole;
bromination of said 3-ethylanisole at a position para to a methoxy group to produce 4-bromo-3-ethyl anisole;
conversion of said 4-bromo-3-ethyl anisole, said conversion comprising (a) reacting said 4-bromo-3-ethyl anisole with n-butyl lithium to produce the lithium salt of the corresponding anion of said 4-bromo-3-ethyl anisole; (b) reacting said lithium salt of the anion of said 4-bromo-3-ethyl anisole with tri-n-butyl borate; and (c) quenching with aqueous acid.

2. A process for the preparation of a compound of Formula I:

I according to Scheme 1, as follows:

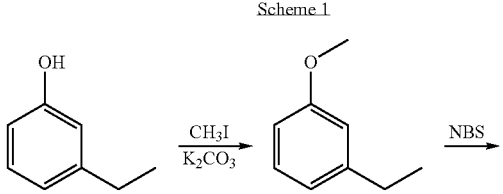

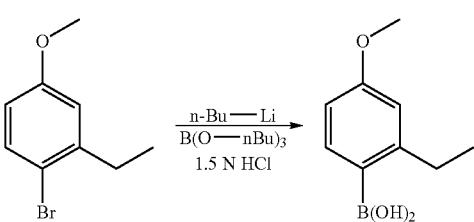

3. A process for the preparation of a compound of Formula II:

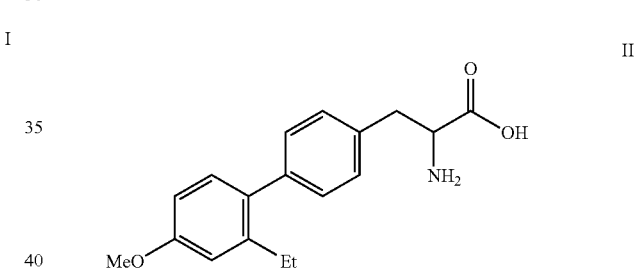

II said process comprising the steps of:
methylation of 3-ethylphenol to produce 3-ethylanisole;
bromination of said 3-ethylanisole at a position para to a methoxy group to produce 4-bromo-3-ethyl anisole;
conversion of said 4-bromo-3-ethyl anisole, said conversion comprising (a) reacting said 4-bromo-3-ethyl anisole with n-butyl lithium to produce the lithium salt of the corresponding anion of said 4-bromo-3-ethyl anisole; (b) reacting said lithium salt of the anion of said 4-bromo-3-ethyl anisole with tri-n-butyl borate; (c) quenching with aqueous acid;
reacting the resultant 2-ethyl-4-methoxy-phenylboronic acid with the triflic anhydride of a suitably protected tyrosine amino acid in the presence of a Palladium catalyst (Suzuki coupling); and
removing the carboxyl protecting group from the resulting biphenyl amino acid to yield the amino-protected amino acid useful for incorporation into a peptide receptor modulator.

* * * * *